United States Patent [19]

Woodward et al.

[11] Patent Number: 5,238,961
[45] Date of Patent: Aug. 24, 1993

[54] PGF 1-ALCOHOLS AND THEIR USE AS OCULAR HYPOTENSIVES

[75] Inventors: David F. Woodward, El Toro; Ming F. Chan, Santa Ana, both of Calif.

[73] Assignee: Allergan, Inc., Irvine, Calif.

[21] Appl. No.: 538,204

[22] Filed: Jun. 14, 1990

[51] Int. Cl.$^5$ ............................................. A61K 31/19
[52] U.S. Cl. ................................... 514/573; 514/913; 514/546; 514/549; 514/552; 514/729
[58] Field of Search ............... 514/573, 913, 546, 549, 514/552, 729

[56] References Cited

U.S. PATENT DOCUMENTS

| | | | |
|---|---|---|---|
| 3,853,854 | 12/1974 | Weinshenker et al. | 260/240 R |
| 3,940,438 | 2/1976 | Weinshenker | 424/317 |
| 3,941,886 | 3/1976 | Weinshenker | 424/317 |
| 4,001,306 | 1/1977 | Morozowich et al. | 260/488 R |
| 4,016,184 | 4/1977 | Morton, Jr. | 260/408 |
| 4,033,989 | 7/1977 | Bundy | 260/408 |
| 4,049,678 | 9/1977 | Peterson | 260/343.41 |
| 4,055,593 | 10/1977 | Weinshenker et al. | 260/514 D |
| 4,060,540 | 11/1977 | Barnady et al. | 260/514 D |
| 4,099,014 | 7/1978 | Peterson | 360/53 |
| 4,256,745 | 3/1981 | Skuballa et al. | 514/317 |
| 4,599,353 | 7/1986 | Bito | 514/530 |
| 4,822,819 | 4/1989 | DeSantis et al. | 514/530 |
| 4,824,857 | 4/1989 | Goh et al. | 514/398 |
| 4,883,819 | 11/1989 | Bito | 514/573 |

FOREIGN PATENT DOCUMENTS

| | | |
|---|---|---|
| 0286903 | 4/1987 | European Pat. Off. |
| 8806448 | 9/1988 | PCT Int'l Appl. |
| 8903384 | 4/1989 | PCT Int'l Appl. |

OTHER PUBLICATIONS

Embase 7601040 (1989). Villumsen et al.
Andersen, Neils *Prostaglandin* 6(5):361–374 (1974).
Bito, *Arch. Ophthalmol.* 105 (1987).
Camras et al., *Invest. Ophthalmol. Vis. Sci.* 16, 1125 (1977).
Gandolfo, C. et al., *Farmaco Ed. Sci.* 27:1125–1129 (1972).
Jenny, Erwin and Schaublin, Peter *Tetrahedron Letters* 26:2235–2238(1974).
Keun Kim, *Investigative Ophthalmology* 14, 36 (1975).
Kondo, Kiyosi et al., *Tetrahedron Letters* 41:3927–3930 (1978).
Maddox et al., *Nature* 273, 549 (1978).
Nillson et al., *Exp. Eye Res.* 48, 707 (1989).
Siebold et al., *Prodrug* 5, 3 (1989).
Starr. *Exp. Eye Res.* 11, 170–177 (1971).
Zajacz et al., *The Eye; Reproduction, Obstetrics and Gynecology* 4, 316 (1976) Chem., Biochem., Pharmacol. Act Prostanoids, INCL. Proc. Symp., Meeting Date 1978, pp. 185–193; ed. Roberts, Stanley N. and Scheinman, Theodore; Pergamon Press (1979).

Primary Examiner—Frederick E. Waddell
Assistant Examiner—Zohreh A. Fay
Attorney, Agent, or Firm—Robert J. Baran; Howard R. Lambert; Martin A. Voet

[57] ABSTRACT

The invention relates to the use of alcohol derivatives of F-type prostaglandins as ocular hypotensives. The PGF derivatives used in accordance with the invention are encompassed by the following structural formula (I)

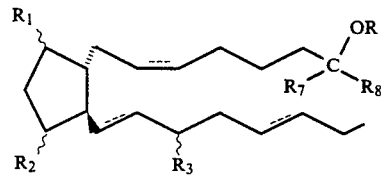

wherein wherein wavy line attachments indicate either the alpha (a) or beta (b) configuration; hatched lines indicate $\alpha$ configuration, solid triangles are used to indicate b configuration, dashed bonds represent a double bond, the 5,6-double bond being in cis-configuration, or a single bond; R is hydrogen or a —(CO)R$_4$ group; R$_1$, R$_2$, and R$_3$ independently are hydroxyl, or —O(CO)R$_5$ groups, wherein R$_4$ and R$_5$ independently stand for saturated or unsaturated acyclic hydrocarbon having from 1 to 20 carbon atoms, or —(CH$_2$)$_n$R$_6$ where n is 0–10 and R$_6$ is an aliphatic, aromatic or heteroaromatic ring, R$_7$ and R$_8$ independently are hydrogen or alkyl of one to 6 carbon atoms or pharmaceutically acceptable salts thereof.

11 Claims, 1 Drawing Sheet

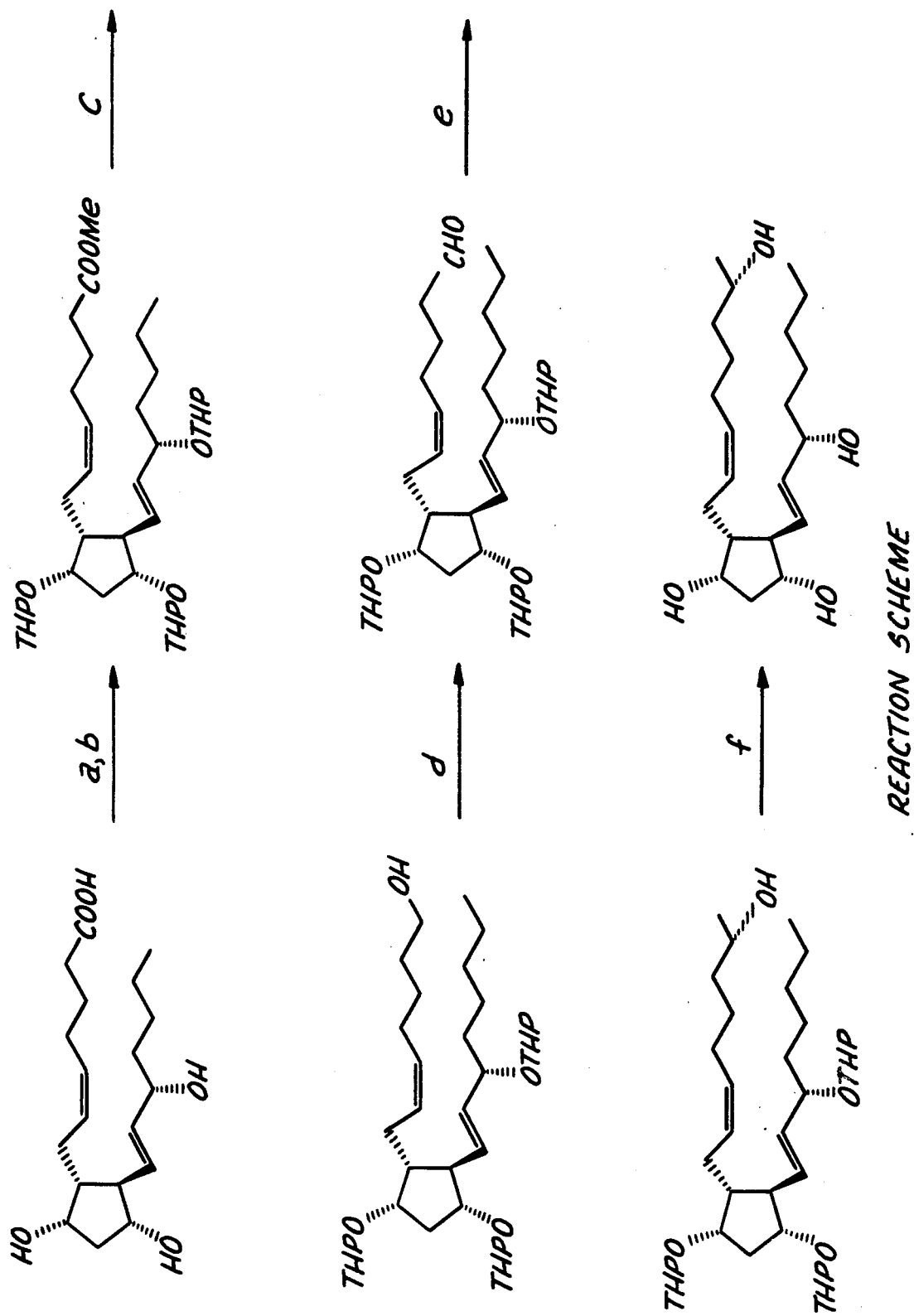
REACTION SCHEME

PGF 1-ALCOHOLS AND THEIR USE AS OCULAR HYPOTENSIVES

FIELD OF THE INVENTION

The present invention relates to prostaglandin 1-alcohols of the F series and their esters. More particularly, the present invention concerns prostaglandin F (PGF) alcohols and esters, that are potent ocular hypotensives, and are particularly suitable for the management of glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which has the following structural formula:

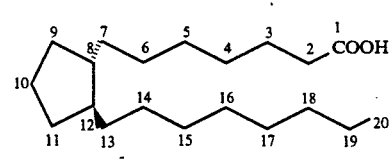

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\alpha}$)].

Prostaglandins were earlier regarded as potent ocular hypertensives, however, evidence accumulated in the last decade shows that some protaglandins are highly effective ocular hypotensive agents, and are ideally suited for the long-term medical management of glaucoma (see, for example, Bito, L. Z. *Biological Protection With Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, presumably as a result of its more effective penetration through the cornea. In 1987 this compound was described as "the most potent ocular hypotensive agent ever reported" [see, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potentials of prostaglandins in the management of conditions associated with increased ocular pressure, e.g. glaucoma are greatly limited by these side effects.

In a series of co-pending U.S. patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed May 25, 1989). Similarly, 11,15- 9,15- and 9,11-diesters of prostaglandins, for example 11,15-dipivaloyl $PGF_{2\alpha}$ are known to have ocular hypotensive activity. See the co-pending patent applications U.S. Ser. Nos. 385,645, 386,312 and 386,834 (all filed Jul. 27, 1989). The disclosures of all of these patent applications are hereby expressly incorporated by reference.

SUMMARY OF THE INVENTION

We have surprisingly found that reduction of the 1-carboxyl group of F-type prostaglandins to —CH$_2$OH provides ocular hypotentives that are distinctly more potent than PGF$_{2\alpha}$ and show a substantially longer duration of activity. Ocular hypertensive diseases may be more effectively and conveniently treated by virtue of the longer duration of these PG compounds, homologs and certain ester derivatives thereof.

The present invention concerns a method of treating ocular hypertension which comprises administering to a mammal having ocular hypertension a therapeutically effective amount of a compound of formula (I)

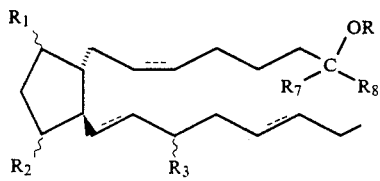

wherein wavy line attachments indicate either the alpha ($\alpha$) or beta ($\beta$) configuration; hatched lines indicate $\alpha$ configuration, solid triangles are used to indicate $\beta$ configuration, dashed bonds represent a double bond or a single bond, the 5,6-double bond being in cis-configuration; R is hydrogen or a —(CO)R$_4$ group; R$_1$, R$_2$, and R$_3$ independently are hydroxyl, or —O(CO)R$_5$ groups, wherein R$_4$ and R$_5$ independently stand for saturated or unsaturated acyclic hydrocarbons having from 1 to 20 carbon atoms, or —(CH$_2$)$_n$R$_6$ where n is 0-10 and R$_6$ is an aliphatic, aromatic or heteroaromatic ring, R$_7$ and R$_8$ independently are hydrogen or alkyl of one to 6 carbon atoms, or a pharmaceutically acceptable salt thereof.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising a container adapted to dispense its contents in metered form; and an ophthalmic solution therein, as hereinabove defined.

BRIEF DESCRIPTION OF THE DRAWINGS

The drawing illustrates a reaction scheme for preparing 1-decarboxyl-1-(1-hydroxyethyl) prostaglandin F$_{2\alpha}$ in accordance with Example 3.

DETAILED DESCRIPTION OF THE INVENTION

The present invention relates to the use of alcohol derivatives of F-type prostaglandins as ocular hypotensives. The PGF derivatives used in accordance with the present invention are encompassed by the following structural formula (I)

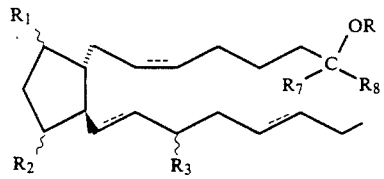

wherein the substituents and symbols are as hereinabove defined. The dotted lines on bonds between carbons 5 and 6 (C-5), between carbons 13 and 14 (C-13) and carbons 17 and 18 (C-17) indicate a single or double bond, of which at least the 5,6-double bond is in cis configuration. If two solid lines are used at C-5, C-13, or C-17, it indicates a specific configuration for that double bond. Hatched lines used at position C-9, C-11 and C-15 indicate the $\alpha$ configuration. If one were to draw the $\beta$ configuration, a solid triangular line would be used at either of these three positions.

A preferred group of the compounds of the present invention includes PGF$_{2\alpha}$ derivatives that have the following structural formula (II)

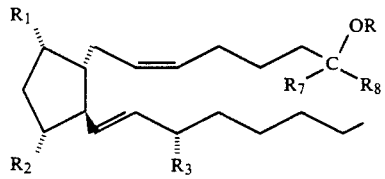

Another preferred group includes PGF$_{3\alpha}$ derivatives having the formula (III)

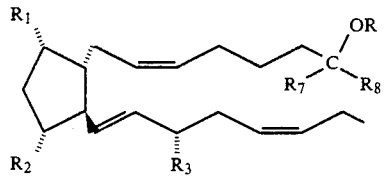

In the above formulae, the substituents and symbols are as hereinabove defined.

The 1-OH compounds and esters of the present invention are known in the art and are, for example, disclosed in the U.S. Pat. No. 4,256,745. The primary alcohols can be conveniently prepared by reduction of the 1-carboxyl group of the corresponding PGF compounds. For example, the reduction of PGF$_{2\alpha}$ methyl ester with diisobutylaluminium hydride in ether at 25° C. is disclosed by Maddox et al., *Nature* 273, 549 (1978).

In general, the reduction may be performed by chemical reducing agents conventionally used for the conversion of carboxylic acids to alcohols. Chemical reducing agents include, but are not restricted to hydrides, such as lithiumaluminium hydride or diisobutylaluminium hydride. As an alternative to direct reduction, the PGF acid may be converted into a corresponding 1-ester before reduction, and the obtained 1-ester may be reduced by chemical reduction.

The hydroxyl group(s) present in any of the positions 9, 11, and 15 are protected from reduction by protecting groups known in the art.

The secondary and tertiary alcohols are usually prepared from the corresponding primary alcohols via oxydation to aldehydes or ketones and subsequent reaction with a suitable Grignard reagent. These reactions are well known in organic chemistry.

Esterification of the PGF 1-alcohols further increases the ocular hypotensive activity, therefore, the compounds of formula (I) in which R is other than hydrogen are particularly preferred.

In a further preferred group of the PGF compounds of formula (I) the hydroxyl groups in the 9, 11 and/or 15 positions are esterified. Particularly preferred are the 11-esters, 15-esters, 11,15-, 9,15- and 9,11-diesters. Esterification in these positions may be performed after the reduction of the 1-carboxyl group with appropriate protection.

The prostaglandin esters according to the present invention can comprise a variety of acyl substituents. In formula (I) $R_4$ and $R_5$ as acyclic hydrocarbons having from one to twenty carbon atoms, inclusive, preferably are straight or branched-chain alkyl, alkenyl or alkynyl groups of one to ten carbon atoms, such as methyl, ethyl, propyl, butyl, pentyl, etc., or an isomeric form thereof; vinyl, propenyl, etc. Most preferably, $R_4$ and/or $R_5$ is —$CH_3$, —$(CH_2)_3CH_3$, —$CH(CH_3)_2$ or —$C(CH_3)_3$.

Alternatively, $R_4$ and $R_5$ can comprise a cyclic component ($R_6$), which preferably is a saturated or unsaturated ring having from three to seven carbon atoms; or an aromatic or heteroaromatic ring, preferably having 5 to 10 carbon atoms and containing oxygen, nitrogen or sulfur as a heteroatom, if present. Preferably, n is an integer between 0 and 4.

In another preferred group of the compounds of Formula (I) $R_7$ and $R_8$ are both hydrogen, or $R_7$ is hydrogen and $R_8$ is alkyl of one to 6, preferably one to four carbon atoms.

A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples.

EXAMPLE 1

Preparation of 1-Decarboxyl-1-Hydroxymethyl Prostaglandin $F_{2\alpha}$

Prostaglandin $F_{2\alpha}$ methyl ester (46.1 mg, 0.125 mmol) was dissolved in methylene chloride (1 ml) and cooled to $-78°$ C. in a dry ice-acetone bath. A solution of diisobutylaluminum hydride (DIBAH) in methylene chloride (1M, 0.75 ml, 0.75 mmol) was then added and the resulting solution was stirred under argon for 1 h. The flask was then placed in an ice bath and allowed to stir for another 6 h. The solvents were then removed under vacuum and the residue was taken up into 5 ml of ethyl acetate and washed with 0.25M sodium hydroxide, water and brine and dried over magnesium sulfate. The ethyl acetate was then removed under vacuum to yield a crude yellow oil which was purified by preparative thin layer chromatography on silica gel using methanol/methylene chloride (2:8) as the eluent. The desired product has an $R_f$ value of 0.23 and weighed 15.3 mg (36% yield).

$^1$H NMR (300 MHz, CDCl$_3$): δ5.3–5.6 (4H, m), 4.17 (1H, distorted t, J=4 Hz), 4.07 (1H, q, J=7 Hz), 3.9–4.0 (1H, m), 3.65 (3H, t, J=6.3 Hz), 3.0–3.2 (1H, br s), 1.2–2.4 (23H, m) and 0.89 ppm (3H, distorted t, J=6.5 Hz). $^{13}$C NMR (75 MHz, CDCl$_3$): δ135.50, 132.88, 130.66, 128.33, 77.66, 73.20, 72.54, 62.28, 55.50, 50.07, 42.78, 37.14, 31.91, 31.75, 26.76, 25.66, 25.37, 25.27, 22.64 and 14.07 ppm.

MS [EI, on tetrakis(trimethylsilyl) ether]: 628 (3.6, M+), 558 (16, M-C$_5$H$_{11}$) 539 (36, M-C$_3$H$_9$OSi) 467 (35 M-C$_5$H$_{11}$-C$_3$H$_9$OSi) 449 [32, M-(C$_3$H9OSi)$_2$], 377 (17), 352 (17), 256 (14), 243 (18), 217 (32), 191 (91), 173 (57), 147 (100), 129 (45) and 117 (15).

HRMS [on tetrakis(trimethylsilyl) ether]:
calcd for C$_{32}$H$_{68}$O$_4$Si: 628.4195.
found: 628.4186.

EXAMPLE 2

Preparation of 1-Decarboxyl-1-Pivaloxymethyl Prostaglandin F$_{2\alpha}$

Prostaglandin F$_{2\alpha}$ methyl ester (158 mg, 0.43 mmol), 3,4-dihydro-2H-pyran (0.4 ml, 4.4 mmol) and pyridinium tosylate (11 mg, 0.04 mmol) were dissolved in methylene chloride (0.45 ml) and stirred at 25° C. for 24 h. The solvents were evaporated and the residue was dissolved in ethyl acetate and washed successively with 10% citric acid, saturated sodium bicarbonate and brine. The organic solution was dried over magnesium sulfate and concentrated. The residue was chromatographed on silica gel (20–40% ethyl acetate in hexanes) to give 437 mg (76%) of prostaglandin F$_{2\alpha}$ methyl ester tris-THP ether ($R_f$ 0.35).

The tris-THP ether obtained from above (401 mg, 0.65 mmol) was dissolved in methylene chloride (1 ml) and cooled to 0° C. in an ice bath. A solution of diisobutylaluminum hydride (1.94 ml of 1.0M solution, 1.94 mmol) in methylene chloride was then added and the resulting solution was stirred under argon for 1 h at 0° C. 0.5M Sodium hydroxide was added and the mixture was extracted with ethyl acetate (3×10 ml). The organic extracts were combined and washed with 10% citric acid, water and brine and dried over magnesium sulfate. The ethyl acetate was then removed under vacuum and the crude product was purified by column chromatography on silica gel using 30–40% ethyl acetate in hexanes as the eluent. The desired product has an $R_f$ value of 0.15 and weighed 219 mg (57%. yield).

The purified alcohol prepared as above (114 mg, 0.193 mmol) was dissolved in pyridine (0.9 ml) and stirred at 0° C. for 10 min. Trimethylacetyl chloride (0.048 ml, 0.386 mmol) was added followed by 4-(dimethylamino)pyridine (1 mg). The mixture was stirred at 0° C. for 1.5 h. The volatiles were evaporated in vacuo. The residue was dissolved in ethyl acetate (20 ml) and washed with 10% citric acid and brine. The organic solution was dried over magnesium sulfate and concentrated to give 138 mg crude product. Purification was achieved by flash chromatography on silica gel using 25% ethyl acetate in hexanes as eluent to give 57 mg (44%) pure pivalate ($R_f$ 0.26).

The product obtained above was stirred with pyridinium tosylate (12.4 mg, 0.05 mmol) in methanol (2 ml) at 25° C. for 18 h and at 50° C. for 4 h. The solvent and volatiles were evaporated and the residue was taken up in ethyl acetate. The organic solution was washed with water and brine, dried over magnesium sulfate and concentrated to give 27 mg crude product. Column chromatography (silica gel, 1% acetic acid in ethyl acetate) gave 16 mg 1-decarboxy-1-pivaloxymethyl PGF$_{2\alpha}$ (44% yield).

$^1$H NMR (300 MHz, CDCl$_3$): δ5.3–5.6 (4H, m), 4.17 (1H, distorted t, J=4 Hz), 4.02 (3H, t, J=6.5 Hz with multiplet underneath), 3.85–3.95 (1H, m), 2.0–2.5 (10H, m), 1.2–1.8 (13H, m), 1.16 (9H, s) and 0.85 ppm (3H, t, J=6.5 Hz).

$^{13}$C NMR (75 MHz, CDCl$_3$): δ179.20, 135.48, 132.86, 130.63, 128.57, 77.98, 73.03, 72.96, 64.10, 55.79, 50.17, 42.67, 38.60, 37.11, 31.55, 28.01, 27.01, 26.54, 25.63, 25.49, 25.01, 22.40 and 13.79 ppm.

IR (CH$_2$Cl$_2$): 1735 cm$^{-1}$.

MS (CI, NH$_3$): m/z 658 (0.4, M+NH$_4$), 641 (M+1, 0.2), 551 (13), 462 (15), 461 (43), 371 (33), 269 (14), 145 (100) and 90 (60).

EXAMPLE 3

Preparation of 1-Decarboxyl-1-(1-hydroxyethyl)prostaglandin F$_{2\alpha}$ (Reaction Scheme 1)

PGF$_{2\alpha}$ methyl ester (prepared from PGF$_{2\alpha}$ and diazomethane, 1.245 g, 3.38 mmol), was dissolved in 3.4 ml CH$_2$Cl$_2$. 1,2-Dihydro-3H-pyran (3.1 ml, 33.8 mmol) was added followed by pyridinium tosylate (85 mg, 0.34 mmol). The reaction was stirred at 25° C. for 19 h and quenched with 10% citric acid. After being extracted into ethyl acetate, the crude product solution was washed with saturated sodium bicarbonate and brine, dried over magnesium sulfate and concentrated to give the crude PGF$_{2\alpha}$ methyl ester, 9,11,15-tris(THP) ether.

A 1.0M solution of diisobutylaluminum hydride in methylene chloride (13.5 ml, 13.5 mmol) was added at −78° C. to the crude product obtained above. The resulting solution was stirred at −78° C. for 4 h and worked up by the addition of a saturated solution of Rochelle salt. The mixture was extracted three times with ethyl acetate. The organic extract was washed with brine and dried over magnesium sulfate. The solvent was evaporated to give 1.99 g of crude product which was chromatographed over silica gel (40–50% ethyl acetate in hexanes) to give 1.81 g pure 1-decarboxyl-1-(hydroxymethyl) PGF$_{2\alpha}$ =9,11,15-tris(THP) ether.

1-Decarboxyl-1-(hydroxymethyl) PGF$_{2\alpha}$ 9,11,15-tris(THP) ether from above was dissolved in 6.1 ml methylene chloride and some finely ground 4A molecular sieves was added. The suspension was stirred at room temperature for 10 min and tetrapropylammonium perruthenate (54 mg, 0.15 mmol) was added. After 10 min at 25° C., the reaction was poured into sodium sulfite solution. The aqueous phase was extracted with ethyl acetate and the organic phase was washed with copper sulfate and brine. The organic phase was dried over magnesium sulfate and concentrated to give 1.852 g of crude product. Flash chromatography on silica gel (40% ethyl acetate in hexanes, $R_f$ 0.51) gave 1.017 g (56% yield) PGF$_{2\alpha}$ 1-aldehyde 9,11,15-tris(THP) ether.

PGF$_{2\alpha}$ 1-aldehyde 9,11,15-tris(THP) ether (72 mg, 0.122 mmol) dissolved in 0.25 ml dry THF was cooled to −78° C. Methyl magnesium bromide in THF (3M, 0.49 ml, 0.147 mmol) was added. The reaction solidified and was allowed to warm to 25° C. and stirred for 1 h. The reaction was worked up with saturated ammonium chloride and extracted three times with ether. The organic extracts were combined and washed with brine and dried over magnesium sulfate. The solvent was removed to give the crude product which was purified by column chromatography to give 47 mg (64% yield) of 1-decarboxyl-1-(1-hydroxyethyl) $PGF_{2\alpha}$ 9,11,15-tris(THP) ether. This product was dissolved in methanol (4 ml) and pyridinium tosylate (20 mg) was added. The solution was heated under argon to 50° C. for 1.75 h and the solvent was evaporated. The residue was taken up in ethyl acetate and washed with citric acid, sodium carbonate and brine, dried and concentrated to give 26 mg of crude product. Purification was achieved with column chromatography (silica gel, 10% methanol in methylene chloride, $R_f$ 0.18) to give 17 mg pure 1-decarboxyl-1-(hydroxymethyl) $PGF_{2\alpha}$ (61% yield) as a mixture of diastereomers.

$^1$H NMR (300 MHz,CDCl$_3$):δ5.51 (1H,1/2AB,-$J_{AB}$=15, $J_{AX}$=6.5 Hz), 5.28-5.43 (3H,m), 4.10 (1H,m), 3.98 (1H,q,J=7 Hz), 3.87 (1H,br s), 3.7-3.8 (1H,m,CH$_3$—C—H—0), 3.1 (3H, very broad s), 1.85-2.35 (6H,m), 1.67 (1H, dd,J=3, 16 Hz), 1.15-1.6 (11H,m), 1.13 (3H,d,J=7 Hz), 0.86 ppm (3H, distorted t, J≈6 Hz);

$^{13}$C NMR (75 MHz, CDCl$_3$):δ136.20, 136.10, 131.30, 131.23, 128.89, 78.06, 73.57, 72.94, 72.85, 68.30 (CH$_3$—CH—0), 67.80 (CH$_3$—CH—0), 55.80, 50.40, 50.30. 43.07. 38.98, 38.76, 37.39, 31.98, 27.45, 27.10, 26.00, 25.88, 25.68, 25.46, 23.68, 22.83. 14.22 ppm;

IR (CHCl$_3$):3620, 3200-3600, 978, 932 cm−1;

MS (EI, TMS derivative):m/z 642 (M+,3%), 552 (24%), 462 (18%), 199 (16%), 173 (52%), 129 (30%), 117 (54%), 102 (100%);

HRMS (EI, TMS derivative): calculated for $C_{33}H_{70}O_4Si_4$:642.4331, found: 642.4341.

EXAMPLE 4

Intraocular Pressure Reducing Activity

Experimental quantities of $PGF_{2\alpha}$-1-OH and its 1-pivaloyl ester and 1-decarboxy-1-(1-hydroxyethyl) prostaglandin $F_{2\alpha}$ were prepared in an ophthalmic formulation containing 0.1% polysorbate (Tween 80)-10 mM TRIS. One eye of each experimental animal was treated by applying one 25 μl drop of the drug formulation to the ocular surface, the contralateral eye received 25 μl of vehicle as a control. Intraocular pressure was measured by applanation pneumatonometry immediately before drug administration and at subsequent, predetermined times thereafter. Rabbits, dogs and cynomolgus monkeys were employed as experimental animals. The data obtained are tabulated as follows (1-4).

By comparing the ocular hypotensive activity of $PGF_{2\alpha}$-1-OH with that of $PGF_{2\alpha}$ in rabbits (Table 1), dogs (Table 2) and monkeys (Table 3), it is clear that $PGF_{2\alpha}$-1-OH is more active. Indeed, $PGF_{2\alpha}$-1-OH is approximately equiactive with $PGF_{2\alpha}$-1-isopropyl ester (Tables 1,2). When $PGF_{2\alpha}$-1-OH is similarly esterified, there is a substantial increase in activity relative to the parent compound (Table 1). Moreover, $PGF_{2\alpha}$-1-pivalate is substantially more active than $PGF_{2\alpha}$-1-isopropyl ester (Table 1). The ocular hypotensive activity of the 1-hydroxyethyl compound is shown in Table 4.

TABLE 1

| RABBIT PROSTANOID | (DOSE %) | EFFECT ON INTRAOCULAR PRESSURE (mmHg) AT PREDETERMINED TIMES POST-ADMINISTRATION | | | | | | | | | |
|---|---|---|---|---|---|---|---|---|---|---|---|
| | | 0 | 0.5 | 1 | 2 | 3 | 4 | 6 | 8 | 10 | 12 |
| $PGF_{2\alpha}$-1-OH | 0.01% | — | — | +8.0** | +2.2 | — | −0.4 | −3.3* | −1.9 | −2.1 | — |
| $PGF_{2\alpha}$-1-OH | 0.1% | — | — | +19.6** | +9.7 | — | −0.75 | −11.4** | −11.5** | −12.0** | — |
| $PGF_{2\alpha}$-1-OH | 1.0% | — | — | +20.9** | +16.1** | — | +3.6 | −9.3** | −12.9** | −11.3** | — |
| $PGF_{2\alpha}$-1-pivalate | 0.001% | — | — | +0.08 | −6.1* | −3.8* | −4.6** | −0.8 | +0.5 | — | |
| $PGF_{2\alpha}$-1-pivalate | 0.01% | — | — | −1.25 | −9.3** | −12.7** | −13.6** | −10.4** | −8.5** | — | |
| $PGF_{2\alpha}$-1-pivalate | 0.1% | — | — | +16.0** | +7.8** | +4.0 | +1.8 | −4.7** | −6.2** | −1.1 | |
| $PGF_{2\alpha}$ | 0.01% | — | — | −1.25 | −2.6* | −1.3 | −1.25 | −0.3 | — | | |
| $PGF_{2\alpha}$ | 0.01% | — | — | +1.25 | −5.0* | −2.1* | −2.9* | +0.9 | — | | |
| $PGF_{2\alpha}$ | 1.0% | — | — | +10.2** | +3.75** | +2.0 | −2.0 | — | | | |
| $PGF_{2\alpha}$-1-isopropyl | 0.01% | — | — | +6.56** | +0.12 | −0.94 | −1.3 | −5.8** | −3.4** | −2.94** | |
| $PGF_{2\alpha}$-1-isopropyl | 0.1% | — | — | +16.7** | +6.75* | −0.7 | −3.2* | −9.7 | −10.1 | −10.0** | | n = 8
*p <0.05
**p <0.01

TABLE 2

| DOG PROSTAGLANDIN | Dose (%) | EFFECT ON INTRAOCULAR PRESSURE (mmHg) AT PREDETERMINED TIMES (HR) POST-ADMINISTRATION | | | | | |
|---|---|---|---|---|---|---|---|
| | | 0 | 1 | 2 | 4 | 6 | 8 |
| $PGF_{2\alpha}$-1-OH | 0.05% | — | −2.7 | −4.3 | −8.0** | −5.1* | −7.0** |
| $PGF_{2\alpha}$ | 0.1% | — | −2.4 | −1.3 | −4.8** | −4.5* | −5.25* |
| $PGF_{2\alpha}$-1-isopropyl ester | 0.1% | — | −3.6 | −2.8** | −6.3* | −9.1 | −10.3 | n = 6
*p <0.05
**p <0.01

TABLE 3

| MONKEY PROSTAGLANDIN | Dose (%) | EFFECT ON INTRAOCULAR PRESSURE (mmHg) AT PREDETERMINED TIMES (HR) POST-ADMINISTRATION | | | | | |
|---|---|---|---|---|---|---|---|
| | | 0 | 1 | 2 | 3 | 4 | 6 |
| $PGF_{2\alpha}$-1-OH | 0.1% | 0 | −1.0 | −2.3** | — | −4.8** | −3.5** |

TABLE 3-continued

| MONKEY PROSTAGLANDIN | Dose (%) | EFFECT ON INTRAOCULAR PRESSURE (mmHg) AT PREDETERMINED TIMES (HR) POST-ADMINISTRATION | | | | | |
| --- | --- | --- | --- | --- | --- | --- | --- |
| | | 0 | 1 | 2 | 3 | 4 | 6 |
| $PGF_{2\alpha}$ | 0.1% | — | −2.0 | −0.6 | — | −2.3 | −2.8 | n = 5-6
**p <0.01

TABLE 4

| Rabbit PROSTANOID | (DOSE %) | EFFECT ON INTRAOCULAR PRESSURE (mmHg) AT PREDETERMINED TIMES POST-ADMINISTRATION | | | | | |
| --- | --- | --- | --- | --- | --- | --- | --- |
| | | 0 | 1 | 2 | 3 | 4 | 6 |
| $PGF_{2\alpha}$-1-hydroxyethyl | 0.01% | | −0.9 | −1.03 | −2.1 | −0.2 | +1.7 |
| $PGF_{2\alpha}$-1-hydroxyethyl | 0.1% | | −2.3 | −6.4** | −4.1** | −4.0** | −3.33** |

*p <0.05
**p <0.01

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

We claim:

1. A method of treating ocular hypertension which comprises administering to a mammal having ocular hypertension an intraocular pressure-lowering amount of a compound of formula (I)

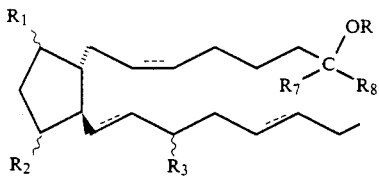

wherein wavy line attachments indicate either the alpha (α) or beta (β) configuration; hatched lines indicate α configuration, solid triangles are used to indicate β configuration, dashed bonds represent a double bond, the 5,6-double bond being in cis-configuration, or a single bond; R is hydrogen or a —(CO)$R_4$ group; $R_1$, $R_2$, and $R_3$ independently are hydroxyl, or —O(CO)$R_5$ groups, wherein $R_4$ and $R_5$ independently stand for saturated or unsaturated acyclic hydrocarbon having from 1 to 20 carbon atoms, or —$(CH_2)_n R_6$ where n is 0–10 and $R_6$ is an aliphatic or aromatic ring, $R_7$ and $R_8$ independently are hydrogen or alkyl of one to 6 carbon atoms or pharmaceutically acceptable salts thereof.

2. The method of claim 1 wherein said compound of formula (I) is selected from the group consisting of $PGF_{2\alpha}$ and $PGF_{3\alpha}$ derivatives.

3. The method of claim 2 wherein R is hydrogen.

4. The method of claim 3 wherein $R_7$ and $R_8$ each is hydrogen.

5. The method of claim 3 wherein $R_7$ is hydrogen and $R_8$ is is alkyl of one to 6 carbon atoms.

6. The method of claim 5 wherein $R_7$ is hydrogen and $R_8$ is alkyl of one to 4 carbon atoms.

7. The method of claim 2 wherein R is —(CO)$R_4$, in which $R_4$ is —C(CH$_3$)$_3$.

8. The method of claim 2 wherein said compound of formula (I) is selected from the group consisting of 1-decarboxyl-1-pivaloxymethyl prostaglandin $F_{2\alpha}$, 1-decarboxyl-1-hydroxymethyl prostaglandin $F_{2\alpha}$, and 1-decarboxyl-1-(1-hydroxyethyl) prostaglandin $F_{2\alpha}$ and pharmaceutically acceptable salts thereof.

9. The method of claim 1 wherein said intraocular pressure-lowering amount is between about 0.001 and about 5% (w/v).

10. The method of claim 9 wherein said intraocular pressure-lowering amount is between about 0.01 and about 1.0% (w/v).

11. The method of claim 4 wherein said intraocular pressure-lowering amount is between about 0.05 and 0.1% (w/v).

* * * * *